United States Patent
Sonnleitner

(10) Patent No.: US 9,562,847 B2
(45) Date of Patent: Feb. 7, 2017

(54) MODULAR ABSORPTION MEASURING SYSTEM

(75) Inventor: Max Sonnleitner, Linz (AT)

(73) Assignee: ASMAG-Holding GmbH, Gruenau im Almtal (AT)

( * ) Notice: Subject to any disclaimer, the term of this patent is extended or adjusted under 35 U.S.C. 154(b) by 894 days.

(21) Appl. No.: 12/936,288

(22) PCT Filed: Apr. 3, 2009

(86) PCT No.: PCT/AT2009/000134
§ 371 (c)(1),
(2), (4) Date: Feb. 25, 2011

(87) PCT Pub. No.: WO2009/121089
PCT Pub. Date: Oct. 8, 2009

(65) Prior Publication Data
US 2011/0141475 A1 Jun. 16, 2011

(30) Foreign Application Priority Data

Apr. 4, 2008 (AT) .................................. A 534/2008

(51) Int. Cl.
*G01N 21/00* (2006.01)
*G01N 21/31* (2006.01)
(Continued)

(52) U.S. Cl.
CPC .............. *G01N 21/31* (2013.01); *G01N 21/78* (2013.01); *G01N 21/783* (2013.01); *G01N 2021/0321* (2013.01); *G01N 2021/0325* (2013.01)

(58) Field of Classification Search
CPC ...... G01N 21/31; G01N 21/78; G01N 21/783; G01N 2021/0321; G01N 2021/0325; G01N 21/03; G01N 2021/158
(Continued)

(56) References Cited

U.S. PATENT DOCUMENTS

| 5,577,137 A | 11/1996 | Groger et al. |
| 5,705,816 A | 1/1998 | Ronge et al. |

(Continued)

FOREIGN PATENT DOCUMENTS

| CN | 1148173 A | 4/1997 |
| CN | 2445323 Y | 8/2001 |

(Continued)

OTHER PUBLICATIONS

International Search Report, PCT/AT2009/000134, dated Aug. 19, 2009.

(Continued)

*Primary Examiner* — Kara E Geisel
*Assistant Examiner* — Dominic J Bologna
(74) *Attorney, Agent, or Firm* — Collard & Roe, P.C.

(57) ABSTRACT

The invention relates to a modular absorption measuring system (1) for fluid media comprising a detection module (2) and a sample module (3), which comprises a sample chamber (14). The detection module (2) comprises a detection system (5), which also comprises an electromagnetic radiation source (8) and a quantum detector (9). The radiation source (8) is designed for supplying light in the direction of the sample chamber (14) and the quantum detector (9) is designed for receiving light from the sample chamber (14). The electromagnetic radiation source (8) is designed as an electroluminescence component and the detection module (2) and the sample module (3) are also designed to be arranged on top of one another.

11 Claims, 6 Drawing Sheets

(51) Int. Cl.
*G01N 21/78* (2006.01)
*G01N 21/03* (2006.01)

(58) Field of Classification Search
USPC .............. 356/440–442, 246, 244; 73/864.91;
250/435–436, 576; 422/82.09; 436/164
See application file for complete search history.

(56) References Cited

U.S. PATENT DOCUMENTS

| | | | | |
|---|---|---|---|---|
| 6,078,705 | A * | 6/2000 | Neuschafer et al. | ........... 385/12 |
| 6,352,630 | B1 * | 3/2002 | Frenkel et al. | .......... 204/403.02 |
| 6,995,348 | B2 | 2/2006 | Bradley et al. | |
| 7,604,981 | B1 * | 10/2009 | Harris et al. | ............... 435/287.2 |
| 2003/0157581 | A1 * | 8/2003 | Grill et al. | ........................ 435/8 |
| 2004/0065806 | A1 * | 4/2004 | Bradley et al. | ............. 250/214.1 |
| 2006/0110283 | A1 * | 5/2006 | Fish | ................................ 422/52 |
| 2006/0240545 | A1 * | 10/2006 | Tomida et al. | ............ 435/289.1 |
| 2007/0102654 | A1 * | 5/2007 | Schoo | ........................... 250/576 |
| 2007/0183936 | A1 * | 8/2007 | Newsam et al. | ............. 422/102 |
| 2008/0200343 | A1 * | 8/2008 | Clemens et al. | ................. 506/9 |
| 2009/0051912 | A1 * | 2/2009 | Salazar et al. | ................ 356/246 |
| 2009/0204271 | A1 * | 8/2009 | Lepschi et al. | ............... 700/300 |

FOREIGN PATENT DOCUMENTS

| | | |
|---|---|---|
| CN | 1508533 A | 6/2004 |
| EP | 1063518 A2 | 12/2000 |
| GB | 2431231 A | 4/2007 |

OTHER PUBLICATIONS

Mao Y et al: "Efficient 4.2 [micro]m light emitting diodes for detecting CO2 at room temperature" Electronics Letters, IEE Stevenage, GB, vol. 32, No. 5, Feb. 29, 1996 (Feb. 29, 1996), pp. 479-480, XP006004794.

* cited by examiner

MODULAR ABSORPTION MEASURING SYSTEM

CROSS REFERENCE TO RELATED APPLICATIONS

The present application is a national phase entry under 35 U.S.C. §371 of International Application No. PCT/AT2009/000134, filed Apr. 3, 2009, published in German, which claims the benefit of Austrian Patent Application No. A534/2008, filed Apr. 4, 2008. The disclosures of said applications are incorporated by reference herein.

BACKGROUND OF THE INVENTION

1. Field of the Invention

The invention relates to a modular absorption measuring system for fluid media comprising a detection module and a sample module, wherein the detection module comprises a detection system, wherein the detection system comprises an electromagnetic radiation source and a quantum detector, wherein the sample module comprises a sample chamber, whereby the radiation source is designed to supply light in the direction of the sample chamber and the quantum detector is designed to receive light from the sample chamber.

2. Description of Related Art

Absorption measuring systems are preferably used in cases where a change in transparency can be used to determine the contents quantitatively. For example, the content of fines can be established in a liquid. Likewise absorption measuring systems are known, in which a sample material is filled into a sample chamber and the latter is evaluated afterwards in a measuring device. Likewise so-called measuring strips are known in which a test section and mostly also a reference section are used, wherein upon the contact of said sections with a sample liquid or in general with a physical/chemical sample a reaction occurs in the reaction section, which is revealed by a colour change or a change in the transparency of the reaction section.

In known devices the problem is also mostly that the sample device and the evaluation device have to be aligned very precisely relative to one another. Small inaccuracies in the alignment can lead to greater differences in the obtained result, which considerably worsens the quality and reliability of repeated measurements for example in a continuous monitoring task.

U.S. Pat. No. 6,995,348 B2 shows for example an optical detection system, in which a sample material in a channel is guided past a plurality of optical detection devices. Each optical detection device is formed in this case by a light source and a detector, which are arranged opposite one another, so that the emitted light passes through the channel and is detected on the opposite side by the detector. As the individual detection devices are arranged along a channel, the disclosed device is designed for example for determining a reaction along the channel. By arranging frequency selective filters in the beam path of each detection device however also an analysis of the sample is possible in different spectral ranges.

As the sample material in the channel passes through all detection devices a selective measurement is not possible for example with the use of a catalyst or an added reagent, as with such a measurement the sample is contaminated by the addition of the additive and thus an additional measurement in a different spectral range or with a different catalyst is usually not possible.

Document US 2007/0102654 A1 discloses an optical sensor, which comprises a detection module consisting of a light-emitting diode and a photodetector, made respectively from an organic semiconducting material. The emitted light passes through the sample holder and is detected by the photodiode. It is also disclosed that an economically attractive alternative to existing sensors is to be found, which is achieved in particular by an integrated structure. Integrated is understood to mean that the sensor is produced in one step, without parts or components of the sensor having to be produced separately, in order to be joined subsequently to the sensor. Both the OLED and the photodiode can be produced directly on a light conductor or a carrier material. The optical sensor comprises for measuring a reference signal a reference photodiode made from an organic semiconductor material, which reference signal originates from the OLED or a second light-emitting diode. Said reference diode is part of a reference module, which has an empty sample holder, in which no sample material is arranged, which sample holder however is passed through by the light of the same reference diode, which also irradiates the sample chamber and the detection photodiode. By means of a light conductor light is directed by the OLED via the sample holder to the photodiode and possibly in addition is directed via the empty sample holder. Furthermore, a non-transparent screen is provided, which should prevent light reaching the photodetector other than through the sample chamber and thus the falsification of the measurement results is prevented. Furthermore, the document discloses a method for producing an optical sensor, whereby an integrated arrangement of the photodiodes and the OLEDs is achieved, in that the latter are arranged on the detection module, whereby the detection module also comprises the sample holder.

Document EP 1 063 518 A2 discloses a device for analysing a gas sample by means of infrared absorption, in which on a common, thermally stabilised carrier, in the immediate vicinity of one another and on one side of the measuring cell, an emitter and a receiver are arranged, whereby the thermal drift of the emitter and the receiver is prevented. To analyse a gas sample by means of infrared absorption it is known that to achieve a measurement that is as precise as possible a long absorption line inside the measuring cell is advantageous. Furthermore, systematically caused fluctuations in the detection characteristics are to be avoided as far as possible. In addition, the emitter and the receiver are arranged on a common, thermally stabilised carrier in the immediate vicinity of one another and on one side of the measuring cuvette. The carrier is in this case a thermally stabilised metal element, on which for direct heating in addition a heating and a control element, for example a transistor, is arranged. Furthermore, an IR-component, for example an IR-photodiode, is provided in the immediate vicinity of the receiver. On the side of the measuring cell opposite the cell window there is a spherical mirror, in order to direct the radiation emitted by the emitter back to the photodiode. By means of direct heating it is possible to keep the carrier and thereby the emitter and the receiver constantly at a temperature of preferably about 55° C. and thus avoid thermally caused drift.

Furthermore, a light-emitting diode is known from the prior art, which has its maximum beam intensity in the region of 4.2 µm wavelength and thus can be used preferably for measuring the absorptions of $CO_2$.

BRIEF SUMMARY OF THE INVENTION

The objective of the invention is to create a measuring device, by means of which it is possible to determine the contents in a sample quantitatively. The objective of the invention is also to design the detection device to be modular, such that an individual configuration is possible with respect to the number of simultaneously performed measurements and the type of measurements. It should be possible to configure the measuring device to make it as fail-safe as possible, whereby the greatest possible measurement precision can be achieved, in particular a high precision of repetitions.

The objective of the invention is achieved in that the electromagnetic radiation source is in the form of an electroluminescence component and the detection module and the sample module are designed to be arranged on top of one another.

The design of the electromagnetic radiation source as an electroluminescence component has the advantage that such components can be produced in a particularly simple manner and compared to other components have a much longer lifetime. As the absorption measuring system according to the invention is preferably designed for single use, all of the components are also designed with regard to the disposal of the measuring system after use. In known devices the electromagnetic radiation source is preferably formed by an organic semiconductor component, in particular by an OLED. However, it is known that organic, light-emitting semiconductor materials have a technologically shorter lifetime. Organic light-emitting diodes have the further disadvantage, that their use is associated with license fees, which is a disadvantage with regard to having an absorption system that is as inexpensive as possible.

The objective of the invention is also achieved in that the detection module and the sample module are designed to be arranged closely on top of one another. It is of considerable importance in the absorption system according to the invention, that two modules are provided, which can be produced separately from one another and independently of one another and are only formed by being arranged on top of one another into a usable absorption measuring system. For the design of a modular absorption measuring systems this is particularly important, as in this way for example a universal detection module can be joined together with a sample module adapted specifically to the sample to be tested to form a measuring system.

A close arrangement of the sample module and the detection module on top of one another is here defined in the sense of close with respect to the fluid medium, whereby the design of the detection and sample module, in particular of the facing flat sides ensures that the arrangement of the detection and sample module forms a secure and reliable sealing of the fluid medium from the environment.

The design according to the invention has the additional advantage that with standardised modules any complex measuring system designed specifically for the samples to be tested can be created. In particular, it is possible for a technician to complete the measuring system on site and adapt it precisely to the measurement requirements, without having to bring along a plurality of different prefabricated measuring systems. This restriction to a few standard components also has significant advantages with regard to the costs of production, as the few components can be produced in large numbers and thus in a particularly inexpensive manner. Furthermore, also the sample chamber is designed as a depression in the same module which has the advantage that said arrangement can be formed by means of a shaping method during the production of the sample module.

In a sample module in a development according to the claims a lead structure is provided for fluid media. Fluid media are defined as all materials which can be transported or moved through a lead structure or a tube arrangement. This includes in particular all fluid media and also gaseous media, whereby the material of the detection and sample module has to be designed for guiding said fluid media. In particular, the temperature and the chemical properties of the medium should not cause any damage to the material of the detection and sample module.

As the samples to be tested may consist of health-damaging substances, all contact with the sample material needs to be avoided. Therefore, the absorption measuring system is preferably designed such that the sample to be tested is directed from a delivery point by means of the lead structure to the area of the sample chamber and is transported away from there in turn. Owing to the modular structure the lead structure can now be designed specifically for the sample material to be transported, in particular the geometrical dimensions of the lead structure can be adapted to the characteristic properties of the fluid medium.

According to one development the lead system is formed as far as possible by groove-like depressions in a flat side of the sample module. This has the particular advantage that the lead structure can be designed by mechanical shaping methods. Preferably, the sample module is designed as an injection moulded part, whereby the lead structure can be designed in the method step for producing the sample module. In particular, in an inexpensive manner a universal sample module can be formed, on which the detection module is arranged, whereby the detection module is designed if necessary specifically for the sample material to be tested Said advantageous developments enable a particularly inexpensive and efficient production of the modular absorption measuring system according to the invention. Optionally however for detailed structuring additional mechanical processing steps can be used, in order for example to form a special lead structure for example.

The absorption measuring system according to the invention is based on determining a change in the transparency of a fluid medium, in order to determine in this way the quantitative proportion of a specific material in the medium. However, a direct determination of a contained substance is not possible, as the transparency will not change or will only change insufficiently with any degree of concentration of the contained substance. Therefore, it is a particular advantage if a reaction material is arranged in the sample chamber. By means of said reaction material it is possible to determine indirectly the quantitative presence of a specific substance in the fluid medium.

The reaction material can be developed for a single measurement, but it is also possible, to perform continual measurements for a specific period. In the first type the reaction material is dissolved by the sample material, so that it is used up by the single measurement. Here the amount of sample material has to correspond exactly to the amount of reaction material. The reaction material could however also be developed such that on contact with the sample material it is not completely dissolved, but dissolves at a constant rate or until reaching a physically/chemically determined concentration. With a correspondingly metered amount of reaction material a measurement is thus possible over a longer period.

In known devices a reaction material mostly has to be introduced in liquid form by means of an active transport system into the reaction chamber. Now in the field of microfluidics active transport means such as pumps or valves are still critical with regard to their tendency to fail.

Therefore, a development according to the claims is particularly advantageous, in which the reaction material is freeze-dried, as thus no active microfluidics are necessary. The freeze-dried reaction material is arranged in the sample chamber and the latter is then sealed tightly. Prior to performing the measurement said seal is removed and the sample module is arranged on the detection module, whereby the modular absorption measuring system according to the invention is ready for use.

By means of the arrangement of a reaction material in the sample chamber there can be an indirect quantitative definition of a substance in the fluid medium, as the reaction material according to the claims is designed for physical/chemical interaction with a substance contained in the fluid medium. For example the reaction material can release a substance into the fluidal medium, which interacts with a component of the contents and there is thus a change in the transparency of the fluid medium. A person skilled in the art also knows how by means of a reaction material a physical/chemical reaction is initiated such that there is a change in the transparency of a fluid medium.

The electromagnetic radiation source emits light in the direction of the sample chamber, which is received by the quantum detector. Possibly the light guide of the fluid medium is not sufficient to direct light guided into the sample chamber so that it can be received by the quantum detector. Therefore, a development is particularly advantageous in which in the sample chamber a light guiding device is arranged. Said light guiding device redirects the light radiated into the sample chamber in order, in particular in the direction of the longitudinal extension of the sample chamber or an optionally arranged reaction material. The optionally weakened light is diverted at the opposite end of the sample chamber by the light guiding device from the sample chamber in the direction of the quantum detector. Said light guiding device can be formed for example by optical reflectors or diffraction devices.

A particularly advantageous development is obtained if the flat side of the detection module and/or the flat side of the sample module has an adhesive layer. As the detection module and the sample module according to the invention are arranged on top of one another, this design has the advantage that by joining together the flat sides an adhesive connection is formed and thus the two modules are joined together to form the absorption measuring system according to the invention. If necessary, the adhesive layer is designed such that by joining together the two modules are connected together in an inseparable manner. The adhesive layer can be formed for example by a bonding agent such as an adhesive. However, it is also possible by means of a solvent to treat the flat sides, such that due to the change in the structure on the arrangement of the modules a localised fusion of the materials occurs.

As the detection or sample module is preferably made of plastic, it is also possible according to one development, to arrange the modules on top of one another by means of a bonding method. In this case without the use of a bonding agent the contact faces are treated thermally such that a microscopic material fusion occurs. A person skilled in art would also be familiar with ultrasound and laser bonding.

It is however also possible to design the detection module to be film-like, so that the latter can be arranged like an adhesive film on the sample module.

A design is advantageous in which the quantum detector is designed as a semiconductor component, as semiconductor components can be adjusted particularly well to the spectral range to be detected.

Furthermore, semiconductor components can also be designed as active components, they thus supply under the influence of electromagnetic radiation for example actively an electric output signal. In one development the semiconductor components could also be in the form of organic semiconductors. Semiconductors made from organic semiconducting material have recently become more important, as to produce such components no energy-intensive processes such as for example high temperature-high vacuum chambers are necessary and thus the components can be produced in a much more inexpensive manner and in a more environmentally friendly manner. In particular, such materials are suitable for use in printing processes, whereby semiconductor components can be produced in a particularly efficient manner.

A development according to the claims is particularly advantageous in which the semiconductor component is designed as an organic semiconductor component. The absorption measuring system according to the invention is preferably designed for single use and is disposed of after use. Also with such one-way devices the main focus is on the unit costs. Organic semiconductors have the crucial advantage that they can be produced in a very inexpensive manner, for example by means of a printing method, and their disposal does not involve excessive effort in order to adhere to environmental guidelines. By means of known methods such as for example inkjet printing, screen printing, stencil printing or pad printing the semiconductor component can be formed without expensive production steps. In particular, no high temperature or high vacuum processes are necessary, as is necessary for the production of inorganic semiconductors. Thus the production is particularly inexpensive and the disposal does not raise any environmental issues, which is particularly advantageous for the one-way absorption measuring system.

A particularly advantageous development is achieved if the radiation source and/or the quantum detector are printed on the first flat side of the detection module. Components that can be applied by printing methods can be produced in particularly simple and inexpensive manner, in particular also an arrangement is possible after the production of the detection module. For example, the prefabricated detection module is inserted into a printing arrangement which afterwards imprints the radiation source and/or the quantum detector. A suitable printing method is for example screen printing, inkjet or stamp printing, whereby other methods are known to a person skilled in the art for printing such components.

Determining the change in transparency in a fluid medium is not only restricted to the optically visible area, but comprises the entire optical area. It is also an advantage for example to increase the measurement precision if a change in transparency can be determined in more than one spectral range. According to the claims therefore the radiation source for the controllable delivery of electromagnetic radiation is formed in at least two spectral ranges, whereby the coverable spectral range comprises in particular the entire optical range. By means of the design according to the claims it is now possible to perform a measurement in a first spectral range, in order to control the radiation source such that it supplies light in a different spectral range, in which the measurement is repeated. In one development the radiation source could also be designed such that it can supply simultaneously the at least two spectral ranges. The quantum detector is photosensitive in those spectral ranges in which the radiation source can supply light.

According to one development the detection module is designed to be transparent at least in some sections. As the detection system is preferably arranged on the second flat side of the detection module, the radiation source thus emits its light through the detection module in the direction of the sample chamber and is received by the quantum detector from the direction of the sample chamber, the detection module is designed to be transparent according to the claims in those sections through which light has to penetrate. This can be achieved for example in that a light conducting material is arranged on the relevant sections during the production of the detection module and afterwards is held and fixed by the material of the surrounding detection module. For example, the surrounding material cannot be designed to be transparent, which has the advantage that interference from external light into the sample chamber is prevented and thus any falsification of the measurement result is prevented as far as possible.

By means of the design according to the invention in which the lead structure comprises at least one structure from a group comprising a collective line, line branching, transport channel, application section, it is ensured that, there is a reliable guiding of the fluid medium in the absorption measuring system. In particular, with regard to a modular structure and a modularised extension said embodiment is also advantageous, as any number of universally designed modules can be lined up next against one another and by means of the lead structure designed according to the claims there is a reliable distribution of the fluid medium.

With regard to continual use and in particular to low maintenance costs one embodiment is advantageous in which the lead structure comprises a coupling device. In this way the absorption measuring system according to the invention for performing the measurement can be coupled easily and rapidly into an existing measuring device and after performing the measurement or after reaching the permissible operating period can be uncoupled from the latter and replaced by a new or updated absorption measuring system.

For the specific guiding of the light from the radiation source into the sample chamber or for guiding the light out of the sample chamber in the direction of the quantum detector one embodiment is advantageous in which the detection module comprises a light guiding device. Said light guiding device is preferably designed such that on arranging the detection module on the sample module it engages in the sample chamber and thus the exit point and thereby the radiation direction of the light can be determined specifically. In particular, in this way a particularly good illumination of the longitudinal direction of the sample chamber is possible. Furthermore, also a particularly good detection and transmission of light out of the sample chamber is possible up to the quantum detector.

In known measuring devices the problem was mostly that the sample device and the evaluation device had to be aligned relative to one another, which was always source of error. In a particularly advantageous development the sample module and/or the detection module comprises a force-locking and/or form-locking receiving device. By means of said receiving device it is ensured that with the arrangement of the detection module on the sample module a correct alignment is achieved, in particular the detection system is aligned precisely in relation to the sample chamber. This development thus ensures that even with repeated measurements any deviations caused by the imprecision of the positioning of the detection module on the sample module are substantially reduced and thus do not influence the measurement result substantially.

For a better understanding of the invention the latter is explained in more detail with reference to the following Figures.

BRIEF DESCRIPTION OF THE DRAWINGS

In a much simplified schematic representation.

DETAILED DESCRIPTION

Figure 1:
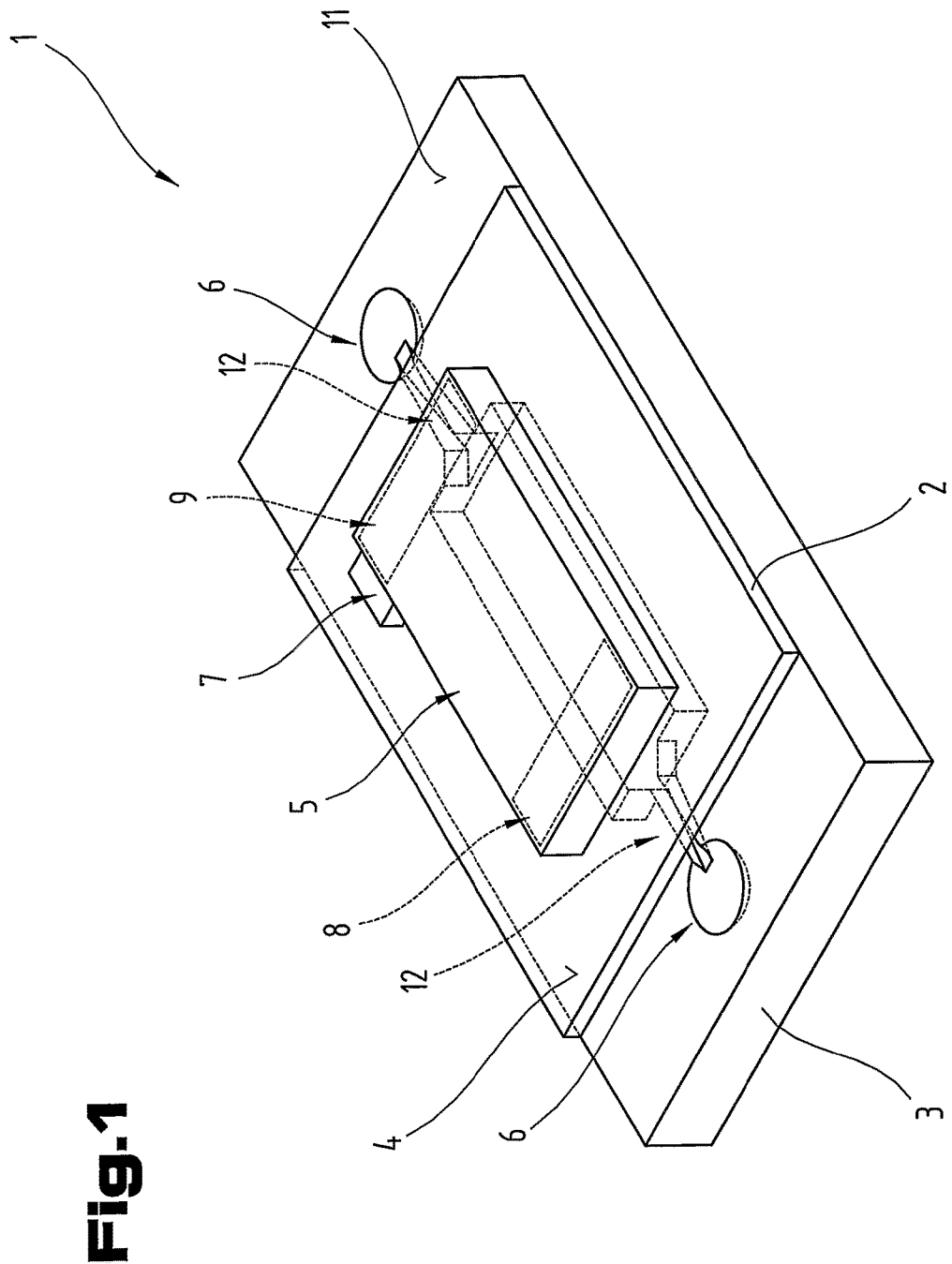
FIG. 1 shows the modular absorption measuring system according to the invention in the arranged state.

First of all, it should be noted that in the variously described exemplary embodiments the same parts have been given the same reference numerals and the same component names, whereby the disclosures contained throughout the entire description can be applied to the same parts with the same reference numerals and same component names. Also details relating to position used in the description, such as e.g. top, bottom, side etc. relate to the currently described and represented figure and in case of a change in position should be adjusted to the new position. Furthermore, also individual features or combinations of features from the various exemplary embodiments shown and described can represent in themselves independent or inventive solutions.

All of the details relating to value ranges in the present description are defined such that the latter include any and all part ranges, e.g. a range of 1 to 10 means that all part ranges, starting from the lower limit of 1 to the upper limit 10 are included, i.e. the whole part range beginning with a lower limit of 1 or above and ending at an upper limit of 10 or less, e.g. 1 to 1.7, or 3.2 to 8.1 or 5.5 to 10.

FIG. 1 shows a perspective view of the absorption measuring system 1 according to the invention, wherein the detection module 2 and the sample module 3 are arranged on top of one another. On the second flat side 4 the detection system 5 is arranged, preferably the latter is imprinted. On the flat side 11 of the sample module 3 coupling devices 6 are arranged, by means of which the transfer of the fluid medium to the lead structure 12 of the absorption measuring system and the takeover of the medium after evaluation are possible. The coupling devices 6 are designed such that a very simple and rapid integration of the absorption measuring systems 1 according to the invention into a testing device is possible. In particular, the absorption measuring system is designed for single use, and has to be replaced after a specific operating time, during which measurements are performed continually. For the electrical contacting of the detection system 5, mostly an electrical contact connection 7 is arranged. The detection system 5 comprises a radiation source 8 for electromagnetic radiation and an electromagnetic quantum detector 9. Preferably, the radiation source 8 is formed by an electroluminescence component, which has the advantage of being inexpensive to produce and can be adapted particularly well to the design of the radiation source. The quantum detector 9 is preferably formed by an organic semiconductor component, for example by a photodetector. The quantum detector is photosensitive at least in the spectral range in which the radiation source emits its light.

According to the invention the detection module 2 and the sample module 3 are arranged on top of one another, whereby only by means of this arrangement is there a contact of the lead structure with the sample chamber. The arrangement is designed such that the outflow of the fluid medium is reliably prevented. For example, the detection module 2 can be designed to be in the form of a film, which is arranged by means of a bonding method on the sample module 3.

Figure 2:
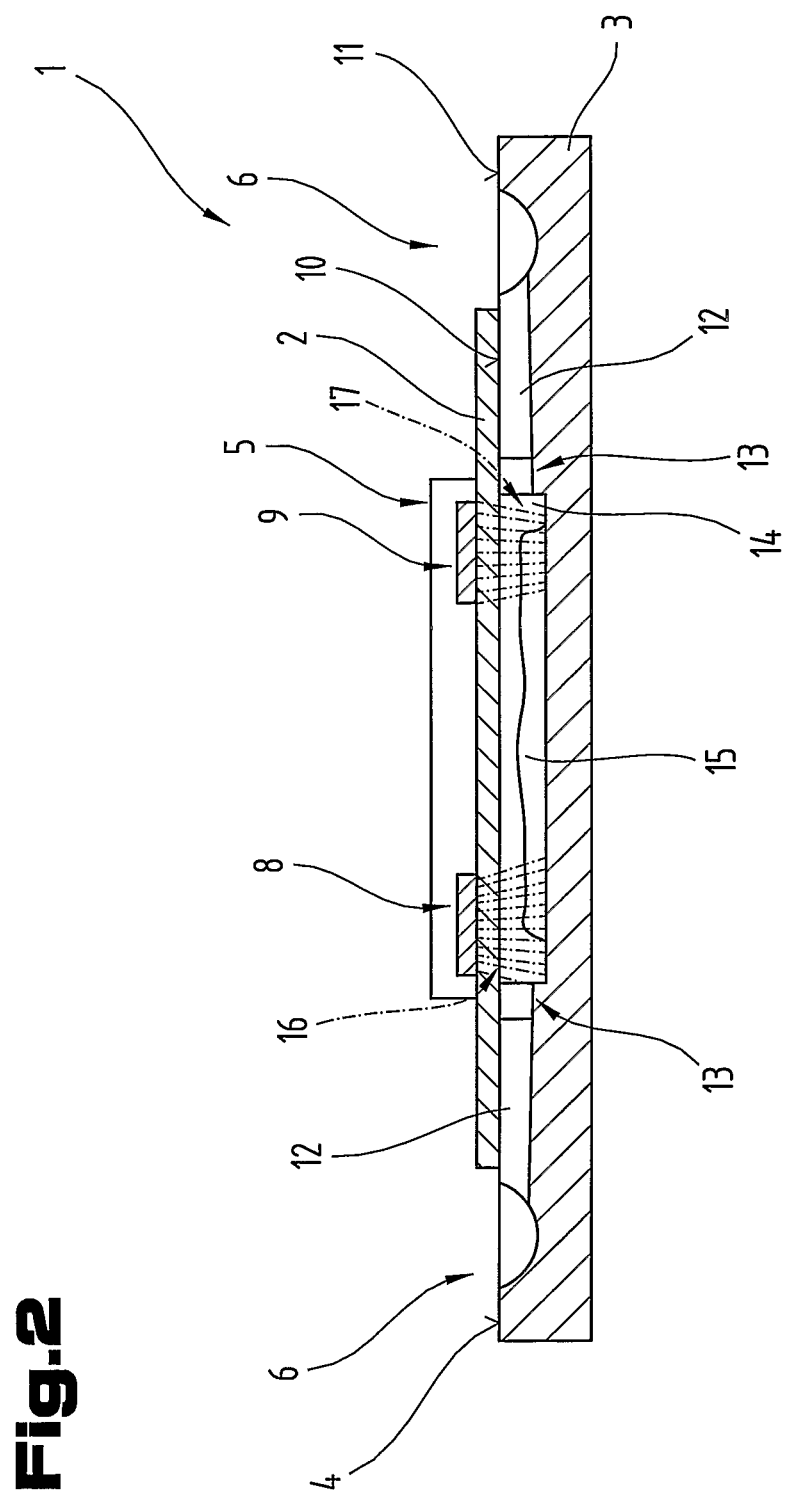
FIG. 2 shows a cross section of the absorption measuring system according to the invention.

FIG. 2 shows a cross section of the modular absorption measuring system 1 according to the invention. It is shown clearly that the detection module 2 with its first flat side 10 is arranged on the flat side 11 of the sample module 3, whereby the arrangement ensures a fluid-tight connection of the detection module 2 and sample module 3, in particular it prevents the fluid medium exiting the lead structure 12 into the environment. The lead structure 12 is now designed such that a fluid medium, which is supplied via the coupling device or an application area 6, is guided in the sample module 3, such that it is transferred in a transfer or takeover section 13 to the sample chamber 14 or is taken over by the latter. In the sample chamber 14 if necessary a further reaction material 15 is provided, which is flowed around by fluid medium, whereby there is a physical chemical reaction with substances in the fluid medium. The reaction material 15 can also optionally supply substances to the fluid medium, which also react with substances in the contents. The radiation source 8 emits light 16 in the direction of the sample chamber 14, whereby there may be a reduction in the light intensity in the sample chamber 14. The returning light 17 is detected by the quantum detector 9 and preferably converted into an electrical output signal. The electrical output signal is evaluated by an evaluation device such that a reduction enables a conclusion to be drawn about the amount of a substance contained in the fluid medium.

The fluid medium is transferred for example on the application section 6 to the lead structure 12, flows through the lead structure 12 to the sample chamber 14, passes through the sample chamber, where there is possibly a reaction with the reaction material 15, leaves the sample chamber again and is directed via the lead structure 12 to the application section 6, from where it is diverted for example into a collecting container. By means of this arrangement the absorption measuring system according to the invention is designed for the continual detection of the absorption values and thus for the quantitative definition of a substance in the contents of the fluid medium.

Figure 3:
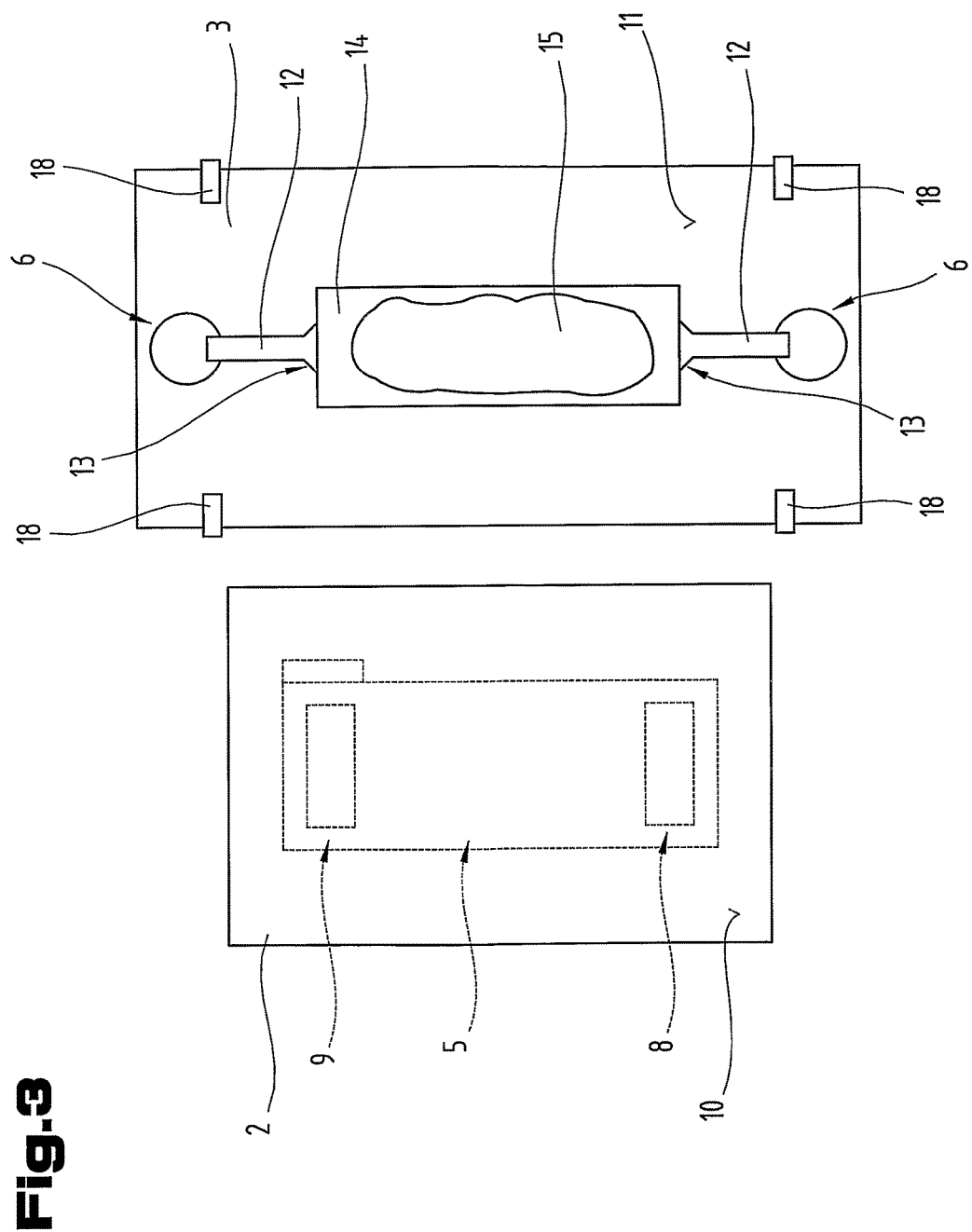
FIG. 3 shows a view of the flat sides of the detection and sample module.

FIG. 3 shows the opened modular absorption measuring system with a top view of the first flat side 10 of the detection modules 2 and the flat side 11 of the sample module 3. The lead structure 12 comprises a transfer or takeover section 13, by means of which a favourable flow transfer or takeover of the fluid medium from the coupling device or application section 6 is ensured via the lead structure 12 into or out of the sample chamber 14. The detection 2 and sample module 3 is in this case designed structurally such that by means of the arrangement of the two modules on top of one another, the detection system 5 is arranged exactly over the sample chamber 14. For this on the sample module 3 a plurality of positioning aids 18 can be arranged, which for example represent a form-closed guide and ensure an exact alignment of the detection module 2 relative to the sample module 3. Preferably, in addition on the first flat side 10 of the detection module 2 or on the flat side 11 of the sample module 3 an adhesive layer is arranged so that on the arrangement of the modules on top of one another, owing to the adhesive effect a connection is formed that is difficult to separate or is inseparable and also in particular the lead structure 12 and the sample chamber 14 are sealed from the environment. For example it is thus possible to produce the detection module 2 and the sample module 3 separately from one another and also to provide them for the user separately, whereby if necessary the arranged adhesive layer is covered by a protective film. Only during the actual use are the protective films removed and the modules arranged on top of one another, whereby an absorption measuring system is formed that is ready for use. The covering with a protective film also has the additional advantage that a sample material 15 in the sample chamber 14, and the lead system 12, remain reliably protected from environmental influences, so that there is no change in the sample material which would influence or falsify the measurement caused by environmental influences. This design has the advantage however, that with a universal detection module 2 and a plurality of different sample modules 3, in particular unlike the reaction material 15, a plurality of specific absorption measuring systems can be formed.

In addition to a described adhesive connection of the two modules 2, 3 a design is also possible in which for example the positioning aids 18 are designed such that they ensure a force-closed arrangement of the modules. For example, the positioning aids 18 could comprise so-called locking connections, which lock automatically on the arrangement of the detection module 2 on the sample module 3 and lock the arrangement tightly.

Figure 4A:
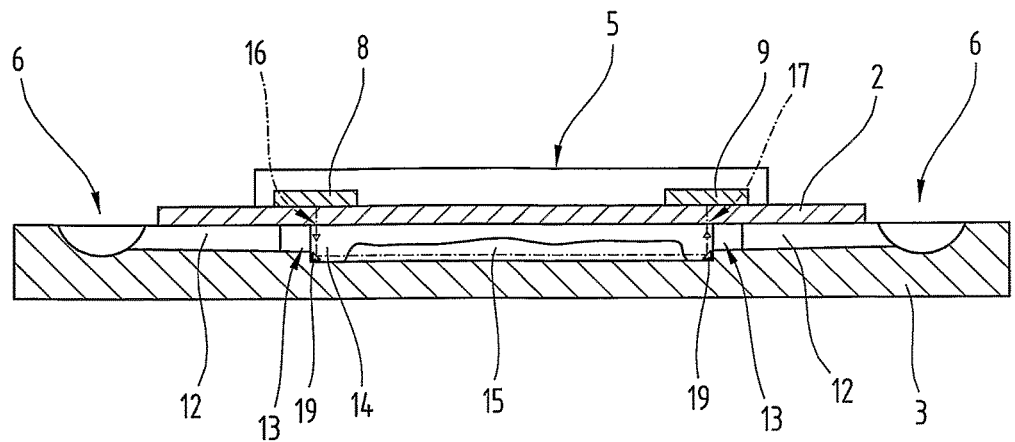
FIG. 4. *a*) and *b*) show possible embodiments of a light guide through the sample chamber of the absorption measuring system.
Figure 4B:
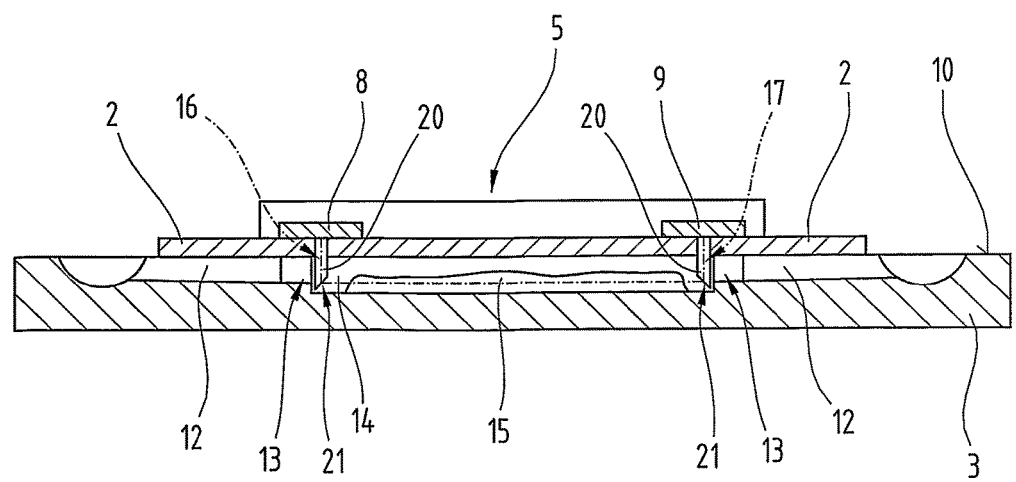

FIGS. 4a and 4b show possible designs of the light guiding through the sample chamber. In FIG. 4a light guiding elements 19 are arranged in the sample chambers 14, which can be formed for example by miniature mirrors. In one development it is also possible however, that the wall of the sample chamber 14 is designed such that, for example by means of surface treatment, a light guiding is achieved. The light guiding elements 19 have the advantage that the incidental light 16 is diverted in the direction of the sample chamber, in particular in the direction of the longitudinal extension of the sample chamber. The possibly weakened light 17 is diverted from the additional light guiding element 19 in turn in the direction of the quantum detector 9.

FIG. 4b shows an additional design of light guiding into the sample chamber. In this case in the detection module 2, respectively in the region of the radiation source 8 and the quantum detector 9, a light conductor 20 is formed. In the drawing the light conductors 20 project beyond the first flat side 10 of the detection module 2, in particular the latter project into the sample chamber 14. The exit areas 21 of the light conductor can be designed for example such that owing to diffraction there is redirection of light into the sample chamber 14. The dimensions of the light conductors 20 in relation to the transfer or takeover section 13 is selected such that there is no reduction in the cross section with regard to the flow-through of the fluid medium.

Figure 5A:
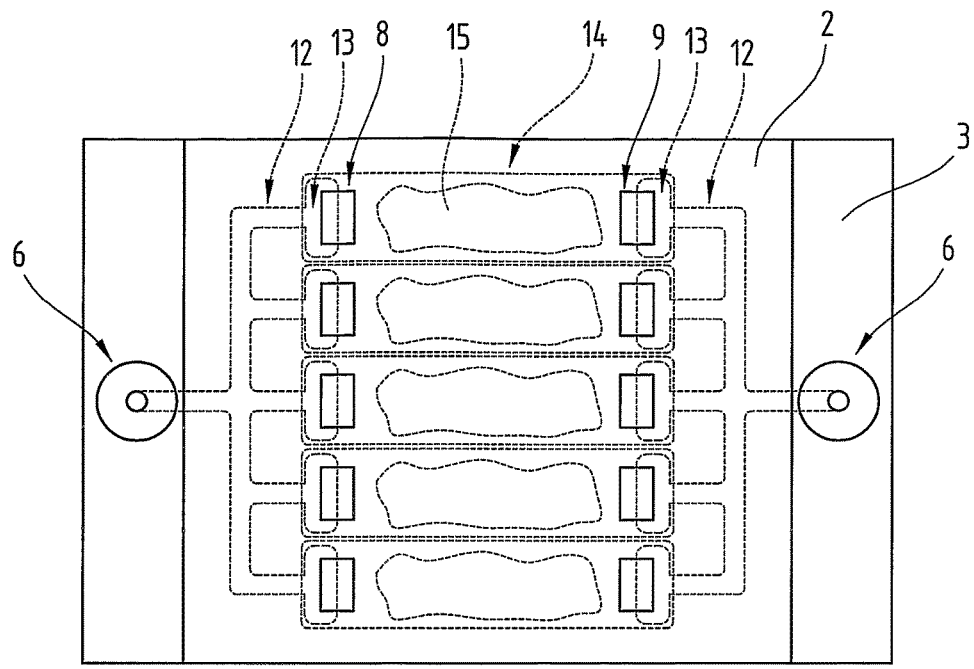
FIG. 5 *a*) *b*) and *c*) show further possible designs of the modular absorption measuring system.

FIG. 5a shows a further design of the absorption measuring system according to the invention in which a plurality of sample chambers 14 are arranged next to one another in the sample module. The sample module 3 comprises a plurality of branchings and lead structures 12, in order to transport the fluid medium from the coupling device or from the application section 6 to the individual sample chambers 14 or away from the latter. This design has the very important advantage that by means of an absorption measuring system at the same time a plurality of different tests can be performed, whereby the sample to be tested is transported via an application section and the line system to the individual test areas or sample chambers. This design can be extended as desired, for example an absorption measuring system can be formed for the analysis of water which can determine continually and simultaneously seventy different sample values.

To determine a reference value and thus to calibrate the absorption measuring systems it is also possible for example that in the lead structure a reference channel is provided, which is flowed through by fluid medium, whereby there is however no reaction with a reaction material. Said basic weakening of the penetrating light beam is used as a reference value for the measurement of the weakening in the additional sample chambers, whereby continually and in particular during continual measurements a reference value can be determined for the prevailing basic weakening. In particular, thus a change in the basic weakening can be determined which would lead unnoticed to a falsification of the result.

Figure 5B:
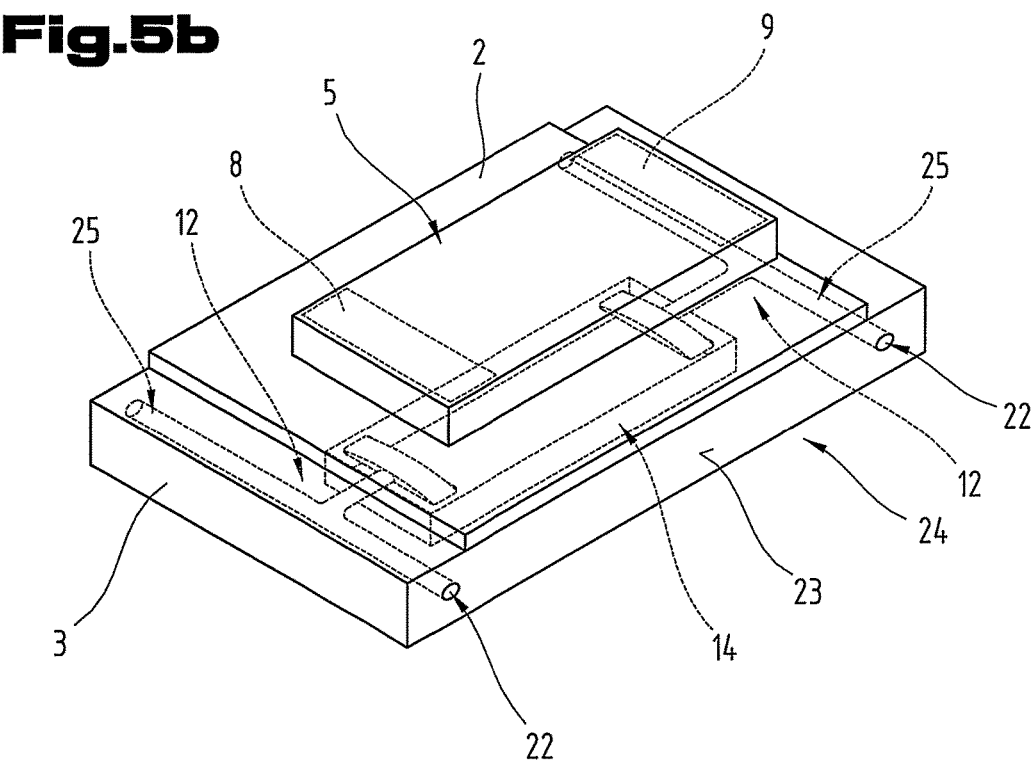

FIG. 5b shows an additional design of the absorption measuring system according to the invention, which has been set up in particular to have a modular structure. In this case the lead structure 12 has been designed such that the access 22 to a distributor line 25 of the lead structure 12 is arranged on a side surface 23 of the sample module 3. The arrangement of the sample chamber 14 and the detection system 5 corresponds to those of the previously described designs. A measuring module 24 designed in this way can be arranged next to another one as many times as desired, whereby access or connections 22 are designed such that by the arrangement of an additional measuring module 24 a sealed connection is formed. If necessary, the connection could also be designed such that the lead structure 12 is tightly sealed to the outside and the connection is only formed by the arrangement of an additional measuring module. It is also possible that on the side surface 23 an adhesive means is applied which is covered for example by a protective film. In the arrangement of an additional measurement module the protective film is removed, the access or connection 22 to the lead structure 12 is thus released and the measuring modules are connected together by means of an adhesive connection. To supply or remove the fluid medium for example at any point a supply module can be provided, which enables the transfer or takeover of the fluid medium to or from the lead structure.

Figure 5C:
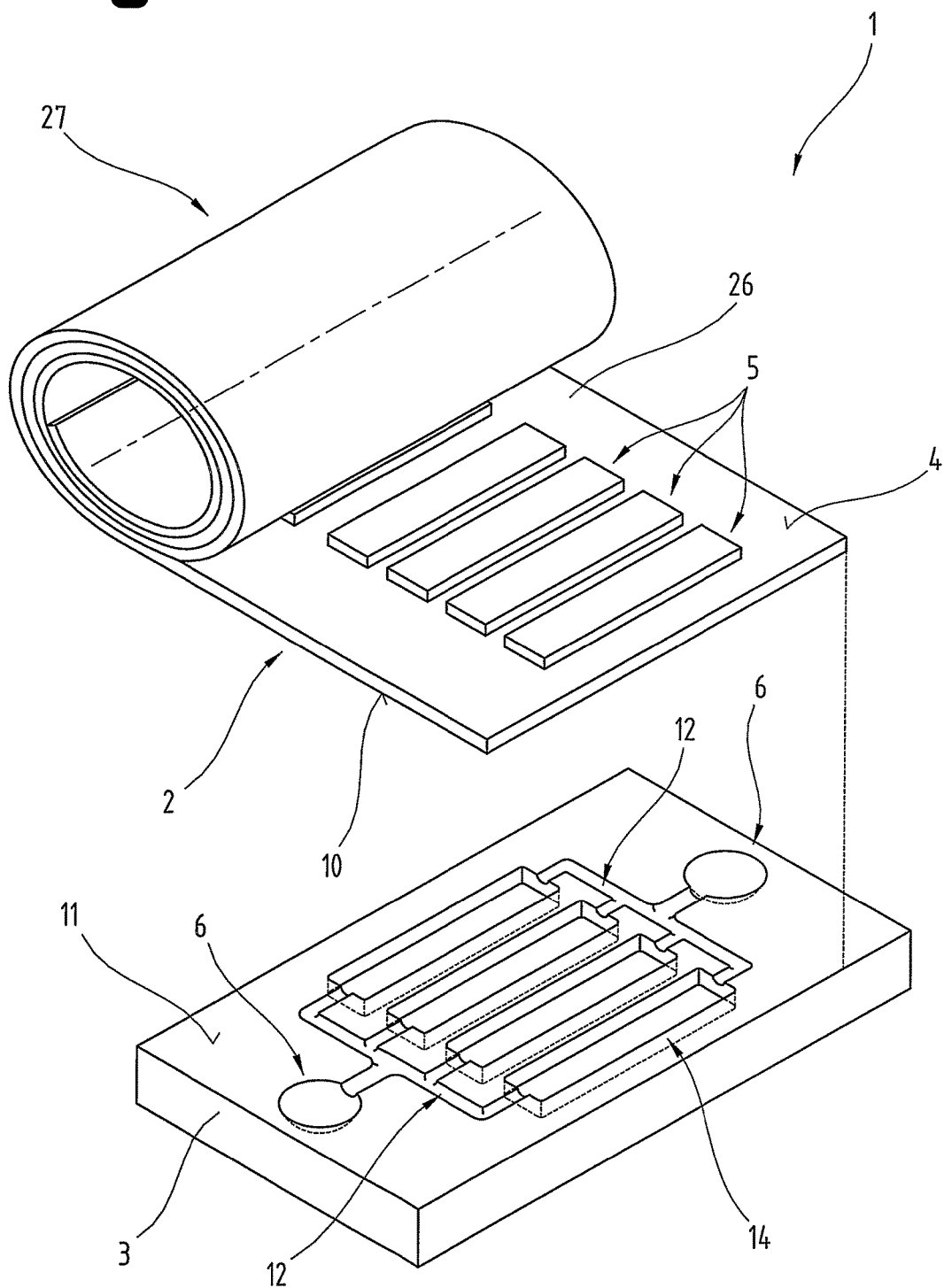

FIG. 5c shows a further possible design of the absorption measuring systems 1 according to the invention in which the detection module 2 is designed to be film-like and is arranged on the sample module 3 or is joined to the latter. In the sample module 3 several sample chambers 14 are provided, which are connected by a lead structure 12 to a coupling device or an application section 6. In the sample chambers 14 if necessary a reaction material can be provided. If necessary, on the flat side 11 of the sample module 3 a protective film can be provided which seals the sample chambers 14, the lead structure and the application section 6 from environmental influences and thus for correct usage maintains the production requirements with respect to purity and protective atmosphere.

According to the invention the detection system 5 comprises an electromagnetic radiation source designed as an electroluminescence component. According to an advantageous development the quantum detector is designed as a semiconductor component, whereby a design as an organic semiconductor component is preferred, so that in a particularly advantageous manner imprinting is possible on a carrier layer. In particular, organic semiconductor components and organic electroluminescence components have the particular advantage that they are flexible, in particular they can be shaped in an elastically restorable manner. Therefore, the detection system 5 can be imprinted onto a flexible flat carrier layer, for example a film material 26, by means of a known printing method such as inkjet printing, screen printing, stamp printing, whereby other possible printing methods are known to a person skilled in the art. The film is designed with respect to its mechanical properties such that it has sufficient strength to carry the detection systems 5 reliably, and that also during correct implementation, in particular on contact with the fluid media, there is sufficient mechanical strength and sufficient chemical stability. The sample module 3 can thus be produced as a so-called meter goods, whereby on the second flat side 4 detection systems 5 are applied continually and spaced apart from one another. As the film material 26 and the detection systems 5 are designed to be flexible, the film can be wound up and as rolled material 27 spread out for use. Preferably, on the first flat side 10 an adhesive layer is applied and covered by a protective film. Prior to the arrangement of the detection module 2 on the sample module 3, the required section of the sample module is determined and separated from the rolled material 27, in particular by cutting. By removing the protective film from the first flat side 10 of the detection module 2 and the flat side 11 of the sample module 3 the two modules can be arranged on top of one another, whereby by means of optionally provided positioning aids an exact alignment of the detection systems 5 is ensured by the sample chambers 14. In particular, by means of this arrangement the lead structure 12 and the sample chambers 14 are sealed from the environment and thus a closed system is provided.

Said embodiment therefore has the particular advantage that a universally produced detection module 2, which is provided in particular unfinished as rolled material 27, can be used for a plurality of differently designed sample modules 3. The design of the detection module 2 as a film with imprinted detection systems 5 has the further special advantage that the latter can be produced particularly inexpensively and efficiently and in particular compared to known devices is much less problematic with regard to environmental impact during production and disposal. Also in relation to user handling on site the design has the advantage, that for each instance of use an optimally adjusted absorption measuring system 1 can be produced, without a plurality of differently finished measuring systems have to be brought along. After the arrangement of the detection module 2 on the sample module 3 the individual detection systems 5 are connected by connection devices, which were also preferably imprinted, to an evaluation device.

The design of the detection module 2 as rolled material 27 can of course also apply to all of the embodiments described above. Also, as already described above, the arrangement or joining of the detection module 2 with the sample module 3 is possible by methods other than adhesion, for example an already mentioned bonding method is possible. This includes all of the methods which are known to a person skilled in the art for joining a film material to a basic body.

The exemplary embodiments show possible embodiment variants of the modular absorption measuring system, whereby it should be noted at this point that the invention is not restricted to the embodiment variants shown in particular, but rather various different combinations of the individual embodiment variants are also possible and this variability, due to the teaching on technical procedure, lies within the ability of a person skilled in the art in this technical field. Thus all conceivable embodiment variants, which are made possible by combining individual details of the embodiment variants shown and described, are also covered by the scope of protection.

FIGS. 4 and 5 show an additional and optionally independent embodiment of the modular absorption measuring systems, whereby the same reference numbers and component names have been used for the same parts as in the preceding FIGS. 1 to 3. To avoid unnecessary repetition reference is made to the detailed description in the preceding FIGS. 1 to 3.

Finally, as a point of formality, it should be noted that for a better understanding of the structure of the modular absorption measuring system the latter and its components have not been represented true to scale in part and/or have been enlarged and/or reduced in size.

The underlying problem addressed by the independent solutions according to the invention can be taken from the description.

Mainly the individual embodiments shown in FIGS. 1 to 5 can form the subject matter of independent solutions according to the invention. The objectives and solutions according to the invention relating thereto can be taken from the detailed descriptions of these figures.

The invention claimed is:

1. A modular absorption measuring system for fluid media comprising:
    (a) a detection module designed as a film, wherein the detection module comprises a detection system that comprises
        an electromagnetic radiation source; and
        a quantum detector, wherein the quantum detector comprises a semiconductor component designed as an organic semiconductor component; and
    (b) a sample module, wherein the sample module comprises:
        a sample chamber designed as a depression in a flat side of the sample module, and
        an injection molded lead structure for fluid media that connects an application section with the sample chamber, wherein the injection molded lead structure comprises groove-like depressions in the flat side of the sample module;
    wherein the sample module including the lead structure and the sample chamber is manufactured in one step,
    wherein a light guiding device comprising an optical reflector or a diffraction device is arranged in the sample chamber,
    wherein the radiation source in the form of an electroluminescence component is designed for supplying light in the direction of the sample chamber and the quantum detector is designed for receiving light from the sample chamber,
    wherein the detection module and the sample module are produced as separate and independent modules designed to be disposed one on top of the other in a sealed arrangement with respect to a fluid medium, and
    wherein the first flat side of the detection module and/or the flat side of the sample module comprises an adhesive layer.

2. The module absorption measuring system according to claim 1, wherein a reaction material is arranged in the sample chamber.

3. The modular absorption measuring system according to claim 2, wherein the reaction material is freeze-dried.

4. The module absorption measuring system according to claim 2, wherein the reaction material is designed for physical/chemical interaction with a substance contained in the fluid medium.

5. The modular absorption measuring system according to claim 1, wherein the radiation source and/or the quantum detector are imprinted on a second flat side of the detection module.

6. The modular absorption measuring system according to claim 1, wherein the radiation source is controllable for the delivery of electromagnetic radiation in at least two spectral ranges.

7. The modular absorption measuring system according to claim 1, wherein the detection module comprises transparent sections.

8. The modular absorption measuring system according to claim 1, wherein the injection molded lead structure comprises at least one structure from a group consisting of a collective line, line branching, and transport channel.

9. The modular absorption system according to claim 1, wherein the injection molded lead structure comprises a coupling device.

10. The modular absorption measuring system according to claim 1, wherein the detection module comprises a light-directing device.

11. The modular measuring system according to claim 1, wherein the sample module and/or the detection module comprises a force-closed and/or form-closed receiving device.

* * * * *